United States Patent [19]

Bauer

[11] Patent Number: 4,664,687

[45] Date of Patent: May 12, 1987

[54] PROCESS FOR THE SEPARATION OF $C_{2+}$, $C_{3+}$ OR $C_{4+}$ HYDROCARBONS

[75] Inventor: Heinz Bauer, Neuried, Fed. Rep. of Germany

[73] Assignee: Linde Aktiengesellschaft, Wiesbaden, Fed. Rep. of Germany

[21] Appl. No.: 809,956

[22] Filed: Dec. 17, 1985

[30] Foreign Application Priority Data

Dec. 17, 1984 [DE] Fed. Rep. of Germany ....... 3445995

[51] Int. Cl.$^4$ ................................................. F25J 3/02
[52] U.S. Cl. ....................................... 62/29; 208/340; 208/341; 62/31; 62/34; 62/38
[58] Field of Search .................... 208/340, 341; 62/29, 62/31, 32, 33, 34, 38, 39

[56] References Cited

U.S. PATENT DOCUMENTS

| | | | |
|---|---|---|---|
| 2,880,592 | 4/1959 | Davison et al. | 62/39 X |
| 3,319,429 | 5/1967 | Pryor | 62/39 X |
| 3,516,261 | 6/1970 | Hoffman | 62/34 X |
| 3,622,504 | 11/1971 | Strum | 208/340 |
| 4,274,850 | 6/1981 | Becker | 62/38 X |
| 4,410,342 | 10/1983 | Horton | 62/39 X |
| 4,453,956 | 6/1984 | Fabbri et al. | 62/34 X |
| 4,456,461 | 6/1984 | Perez | 62/34 X |
| 4,479,871 | 10/1984 | Panade et al. | 208/340 |
| 4,486,209 | 12/1984 | Fabbri et al. | 62/34 X |
| 4,519,824 | 5/1985 | Huebel | 62/34 X |

Primary Examiner—Glenn Caldarola
Attorney, Agent, or Firm—Millen & White

[57] ABSTRACT

In a process for the separation of $C_{2+}$, $C_{3+}$ or $C_{4+}$ hydrocarbons from a gas stream containing light hydrocarbons and, if desired, of components boiling lower than methane, in which the gas stream, being under an elevated pressure, is cooled, partially condensed and separated in a phase separator into a liquid and a gaseous fraction; the gaseous fraction is engine expanded, and the liquid fraction is fractionated by rectification into a product stream containing substantially $C_{2+}$, $C_{3+}$ or $C_{4+}$ hydrocarbons and a residual gas stream containing predominantly lower boiling components, the improvement comprising subjecting the gaseous fraction forming after partial condensation, before engine expansion thereof, to heat exchange with the engine expanded gaseous fraction, thereby cooling said gaseous fraction and separating additional components which condense out before the engine expansion stage.

22 Claims, 7 Drawing Figures

PROCESS FOR THE SEPARATION OF $C_{2+}$, $C_{3+}$ OR $C_{4+}$ HYDROCARBONS

CROSS REFERENCE TO RELATED APPLICATIONS

This application is related to concurrently filed and commonly assigned applications entitled "Separation of $C_{3+}$ Hydrocarbons by Absorption and Rectification," Sapper Ser. No. 809,953; "Process for Separation of $C_{2+}$ or $C_{3+}$ Hydrocarbons," Bauer Ser. No. 809,958; and "Process for the Separation of $C_{2+}$ or $C_{3+}$ Hydrocarbons from a Pressurized Hydrocarbon Stream," Bauer, Ser. No. 809,957, said applications being incorporated by reference herein.

BACKGROUND OF THE INVENTION

This invention relates to a process for the separation of $C_{2+}$, $C_{3+}$ or $C_{4+}$ hydrocarbons from a gas stream containing light hydrocarbons and, if desired, of components boiling lower than methane, in which the gas stream, being under an elevated pressure, is cooled, partially condensed and separated into a liquid and a gaseous fraction, and wherein the gaseous fraction is engine expanded (expansion while performing external work—also called work expansion) and the liquid fraction is fractionated by rectification into a product stream containing substantially $C_{2+}$, $C_{3+}$ or $C_{4+}$ hydrocarbons and a residual gas stream containing mostly lower boiling components.

Such processes are particularly useful for the separation of ethane, propane or butane from natural gases or other gases, e.g., refinery gases. Further, these processes are suitable for the separation of similar unsaturated hydrocarbons, i.e., for examples, ethylene, propylene or butylene, provided these components are contained in the gas stream to be fractionated, which is the case for refinery gases. The reprocessing of refinery gases has recently become attractive since market process for LPG ($C_3/C_4$ hydrocarbon mixture) have risen, while, on the other hand, vacuum residues and heavy oil are hard to sell. For this reason, the hard to sell heavy products are burned to cover the internal fuel needs of a refinery, while the easily salable $C_{3+}$ hydrocarbons are separated from refinery gases especially those which collect in large amounts during processing of light crude oil components into gasoline.

A process of this kind is described in an earlier German patent application No. P 34 08 760.5 filed Mar. 9, 1984 in Germany, having a common assignee, and corresponding substantially to U.S. application Ser. No. 709,742 filed Mar. 8, 1985 by Bauer et al, said U.S. application being incorporated by reference herein.

A major feature of this previously filed U.S. application is that the cold, i.e., refrigeration obtained during engine expansion of the gaseous fraction remaining after partial condensation, is used not for the production of reflux liquid in the rectification column, but for the cooling and partial condensation of the crude gas. Therefore, it is no longer necessary to feed the light components of the gas stream into the rectification column. Elimination of the introduction of the light components present in the feedstock stream (e.g., hydrogen, as well as $C_1$ and, if desired, $C_2$ hydrocarbons present in refinery gases; or nitrogen, as well as $C_1$ and if desired, $C_2$ hydrocarbons in natural gases) into the separation column makes it possible to perform the rectification at a higher temperature, e.g., about 160° to 300° K., level of the overhead condensor. The possibility of using a simple and inexpensive external refrigeration cycle for cooling of the overhead in the rectification column provide a considerable improvement in carrying out the aforementioned process. Further improvement is nevertheless still desirable.

SUMMARY OF THE INVENTION

Therefore, an object of one aspect of this invention is to provide a process of the aforementioned type wherein the separation of the $C_{2+}$, $C_{3+}$ or $C_{4+}$ hydrocarbons is made possible in a more economic manner.

Upon further study of the specification and appended claims, further objects and advantages of this invention will become apparent to those skilled in the art.

This object is achieved in a process for the separation of $C_{2+}$, $C_{3+}$ or $C_{4+}$ hydrocarbons from a gas stream containing light hydrocarbons and, if desired, of components boiling lower than methane, in which the gas stream, being under an elevated pressure, is cooled, partially condensed and separated in a phase separator into a liquid and a gaseous fraction; the gaseous fraction is engine expanded, and the liquid fraction is fractionated by rectification into a product stream containing substantially $C_{2+}$, $C_{3+}$ or $C_{4+}$ hydrocarbons and a residual gas stream containing predominantly lower boiling components, wherein the improvement comprises subjecting the gaseous friction forming after partial condensation, before engine expansion thereof, to heat exchange with the engine expanded gaseous fraction, thereby cooling said gaseous fraction and separating additional components which condense out before the engine expansion stage.

According to the process of the invention, the engine expanded fraction is not immediately heated by heat exchange with the gas stream that is to be fractionated, but first provides for heat exchange only with the uncondensed portion, e.g., the gaseout fraction of the gas stream. Thus, the desired peak cold produced by the engine expansion is introduced into the gaseous fraction, contributing in a particularly advantageous way to an increased condensate formation, thus leading to a higher yield of $C_{2+}$, $C_{3+}$ or $C_{4+}$ hydrocarbons. This process also avoids a subcooling of the condensed portions of the gas stream to be fractionated, which is an energy wasteful operation.

In a further embodiment of the invention, which is particularly useful for the separation of $C_{2+}$ or $C_{3+}$ hydrocarbons, the heat transfer between the unexpanded and expanded gaseous fraction is performed in a mass transfer column having at least two equilibrium stages. Separation of the liquid fraction formed during partial condensation also takes place in the same column, whereby the partially condensed gas stream is fed to the lower region of the column and the heat exchange between the unexpanded and expanded gaseous fractions occurs in the upper region of the column. Feeding the partially condensed gas stream into the lower region of the column inherently produces a heat input in the bottom of the column, wherein the light components dissolved in the liquid fraction are at least partially removed, i.e., stripped out, and thus are kept away from the rectification stage. The heat exchange occurring in the column head between the cold, expanded fraction and the warmer, unexpanded gaseous fraction, however, causes a cooling of the head, which results in an increased condensation of the higher boiling components of the gaseous fraction, and thus produces a better yield.

This particular embodiment normally requires in the upper region of the phase separator utilized after the partial condensation, the installation of a coiled heat exchanger, or the like, thereby enabling a heat exchange and mass transfer to be performed in this region. For embodiments involving the processing of very great amounts of gas, the investment expenses required for this installation may become so high that in many cases another embodiment of the invention will prove to be more suitable.

According to this embodiment it is also provided that, first, the further cooling of the gaseous fraction takes place in a heat exchanger which is structurally separate from the separator used for the phase separation, and second, that the phase separation occurring after the partial condensation and the phase separation of the additionally condensed components take place in separate separators. The additional components which condense out are then returned after their separate separation to the phase separator used for the phase separation after said partial condensation.

Although this embodiment of the invention requires an additional phase separator, it is less expensive in large installations since, instead of an expensive coiled heat exchanger, or the like, in the upper region of the separator, the further cooling of the gaseous fraction preferably takes place in a comparatively inexpensive, plate heat exchanger as described, for example, in Perry's Chemical Engineer's Handbook, 5th Edition, McGraw-Hill, p. 11-22. Also, this embodiment has the further advantage of being better suited for the separation of $C_{4+}$ hydrocarbons, independent of the size of the installation, than the previously described embodiments of the invention.

In a further variation of this embodiment, it is provided that the additional components condensed out are recycled to the upper region of the separator which is provided for the phase separation after the partial condensation. The components pass through the separator, countercurrent to the rising gaseous fraction, whereby a mass transfer between the two streams takes place. The light components present in this additional condensate, evaporate, and at the saem time the heavy components condense out of the rising gas phase.

Since in this embodiment, the reflux sent to the rectification stage is formed apart from the phase separator and not directly in the separator, advantages result in this embodiment in regard to the reflux ratios in the separator, particularly the fact that the complete amount of reflux amount is delivered at the lower temperature.

To avoid thermal losses in the separator, in a further embodiment of the invention it is advantageous for the additional components condensing out be reheated, e.g., about 10° to 70° K. before reflux into the separator. Thus, in the separator essentially only a mass transfer, with minimal heat exchange takes place. It is preferred that the additional components which condense out are heated at least to the boiling point. This can take place, for example, in the heat exchange with the gaseous fraction that is to be further cooled, before its engine expansion.

In a particularly preferred embodiment of the process the residual gas stream collecting during the rectification, i.e., the overhead stream is fed into the gaseous fraction collecting after partial condensation, and the resulting mixture is engine expanded, before it is heated in the heat exchanger by heat transfer with the gas stream that is to be fractionated. By such a procedure, not only is a greater cooling performance obtained by the engine expansion of the residual gas from the rectification than by the conventional simple expansion in a throttle valve, but also, the admixing of the residual gas with the gaseous fraction separated from the condensed feed gas stream results in an improved efficiency of the expansion turbine utilized for the expansion. This is believed due to the fact that the residual gas stream from the rectification stage has a higher molecular weight than the gaseous fraction.

After the separation of the gas stream into a liquid and a gaseous fraction, the resulting gaseous fraction, like the residual gas removed from the head of the rectification, is substantially at its dew point. In the mixing of these two fractions, both at their dew points, condensate formation typically occurs. According to an additional embodiment of the invention, the formed condensate is separated before engine expansion, so as to guarantee a more reliable operation, i.e., liquid free of the expansion turbine. The condensate separation is achieved in a particularly simple way, due to the fact that the residual gas is also fed into the column, whereby the residual gas fraction can flow both above and below the heat exchanger used for the expanded gaseous fraction. However, condensate formation can also be avoided by the fact that the gaseous fraction and/or the residual gas stream and/or the mixture coming from the column is heated to an effective temperature in a heat exchanger before engine expansion so that the mixture temperature is not below the dew point of the mixture.

In the processing of feed gas streams which are rich in components boiling lower than methane, it is provided in an embodiment of the invention that a concentration of these low boiling components take place, for which purpose they are first separated by another partial condensation before the engine expansion of the gaseous fraction which has been separated from the condensed $C_1$ and $C_2$ hydrocarbons. This procedure can also be used in the separation of $C_{2+}$ or $C_{3+}$ hydrocarbons and of nitrogen from nitrogen-rich natural gas or, particularly, for obtaining the heavy hydrocarbons and hydrogen from hydrogen-rich refinery gases and the like. Such a separation is particularly advantageous if the feedstock stream exhibits a relatively high proportion of low boiling components, for example, a hydrogen content on the order of magnitude of 50 to 90%. Such an amount of hydrogen is sufficient to produce the cold necessary for additional separation by expansion, without additional external energy having to be used.

In many applications, a further fractionation of the $C_{2+}$, $C_{3+}$ or $C_{4+}$ hydrocarbon products, particularly a separation between a $C_3/C_4$ hydrocarbon mixture and the $C_{5+}$ hydrocarbons, is desirable. For this purpose, according to another preferred embodiment of the process, the major part, e.g., 50 to 90% of the $C_{5+}$ hydrocarbons are separated from the gas stream before the formation of the phase separated liquid and gaseous fractions, provided the concentration of these components is great enough, typically about 1 to 10% of the stream, that such a separation is worthwhile.

The $C_{5+}$ separation preferably takes place by partial condensation at a temperature, e.g., about 240° to 280° K., which is above the temperature at which the above described liquid and gaseous fractions are formed. By the earlier separation of heavy components, the resulting mixture fed to the rectification is almost free of $C_{5+}$ hydrocarbons, so that in the following rectification of the liquid fraction, a product stream is obtained, which after a $C_{3+}$ separation forms a commercial LPG fraction.

To raise the yield of $C_3$ and $C_4$ hydrocarbons, it is proposed in a further embodiment of the process that the separated heavy hydrocarbons also be fed to the rectification stage, whereby the feed of the $C_{5+}$ fraction into a rectification column at a suitable equilibrium plate takes place below the feed location of the liquid fraction formed during partial condensation, and it is further provided to remove a stream containing substantially only $C_3$ and $C_4$ hydrocarbons between the two feed streams. By the additional rectification of the $C_{5+}$ fraction, the $C_3/C_4$ hydrocarbons, which dissolved in the liquid phase during formation of the condensed $C_{5+}$ fraction, can also be easily recovered as a product. A region of maximum of $C_3/C_4$ concentration is formed in the rectification column between the two feed stream locations, and this is where the $C_3/C_4$ product stream is advantageously removed.

BRIEF DESCRIPTION OF THE DRAWINGS

Various other objects, features and attendant advantages of the present invention will become more fully appreciated as the same becomes better understood when considered in conjunction with the accompanying achematic flowsheets, in which like reference characters designate the same or similar parts throughout the depicted preferred embodiments, and wherein.

DETAILED DESCRIPTION

Figure 1:
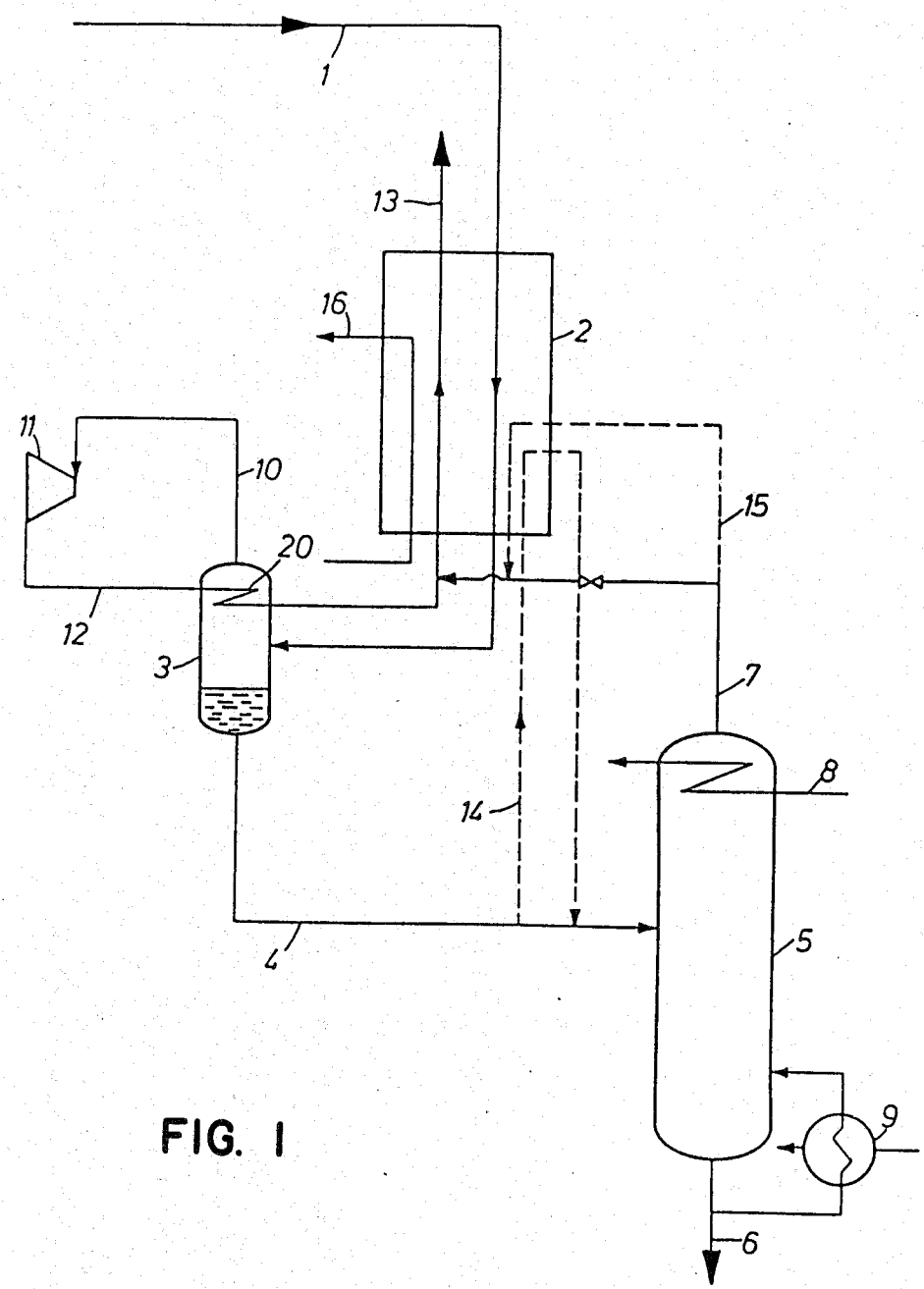
FIG. 1, is a relatively simple embodiment of the process.

In the embodiment shown in FIG. 1, the gas stream to be fractionated and which is under elevated pressure and at approximately ambient temperature is fed by pipe 1 to heat exchanger 2, in which it is cooled to such an extent that most of the hydrocarbons to be separated, in other words, the $C_{2+}$, $C_{3+}$ or $C_{4+}$ hydrocarbons, are condensed therefrom. The partially condensed gas stream is subjected to a phase separation in separator 3, in which the condensate is fed by pipe 4 to a rectification column 5, in which it is fractionated into a $C_{2+}$, $C_{3+}$ or $C_{4+}$ fraction, which is removed as a product stream by pipe 6 from the bottom of the column, and into a residual gas stream 7 containing lower boiling components. The rectification is performed by use of a head cooling 8 operated with external cold as well as, for example, a bottom heating unit 9 heated with low-pressure steam or hot water, in which a partial stream of the bottoms product, branches off of product pipe 6, is heated and then returned to the column bottoms.

The gaseous fraction remaining in separator 3 after separation of the condensate, before it is fed to expansion turbine 11 by pipe 10, is again cooled, e.g., to about 150° to 250° K., in the upper region of separator 3 by indirect heat exchange with the engine expanded gaseous fraction in heat exchanger 20. The heavy components fall into the lower region of separator 3, countercurrent to the rising gaseous fraction. Heat exchanger 20 is preferably a suitably coiled heat exchanger, as a result of which a process is provided that corresponds to the installing of a desired number of mass transfer plates.

The additionally cooled condensate-free gaseous fraction is finally fed by pipe 10 to expansion turbine 11 and, after engine expansion, is removed at the lowest, e.g., about 120° to 230° K. process temperature by pipe 12. After heating in heat exchanger 20, this gas is mixed with the residual gas of the rectification from pipe 7 and is heated to approximately ambient temperature in heat exchanger 2, before it is removed by pipe 13 as residual gas.

The streams removed by pipe 4 and 10 from separator 3 or by pipe 7 from rectification column 5 can, if desired, be heated or cooled, which, e.g., can take plate in heat exchanger 2, to suitable temperature levels before their further processing. This is indicated by dash lines 14 and 15 for the streams in pipes 4 and 7. The external cold requirement for the process is covered by a cooling circuit, which is indicated diagrammatically by 16, and the cooling of the gas mixture is performed in heat exchanger 2 together with the process streams to be heated.

Figure 2:
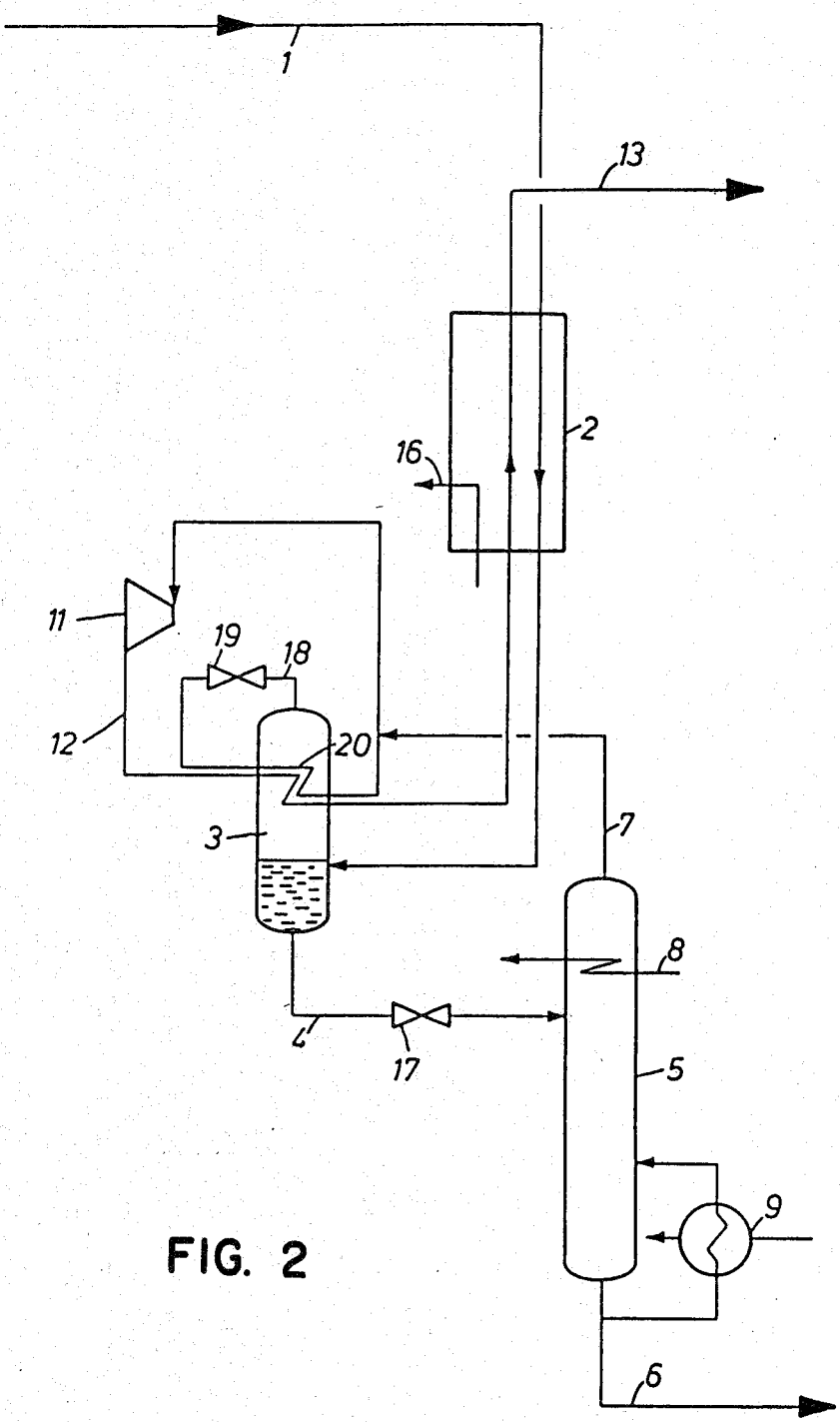
FIG. 2, is a first embodiment of the process in which the pressure of the gas mixture to be fractionated is higher than the rectification column pressure.

In the embodiment disclosed in FIG. 2 the gas stream in pipe 1 which is to be fractionated is under a relatively high pressure, e.g., 1 to 30 bar greater than that in rectification unit 5. After separation of the condensate in separator 3, this condensate is expanded to the rectification pressure in a throttle valve 17 before being fed into rectification column 5. The gaseous fraction is removed from separator 3 by pipe 18, expanded in valve 19 to the pressure of the residual gas in pipe 17 and, after heating in heat exchanger 20 against the still unexpanded gaseous fraction, e.g., to about 170° to 250° K., is mixed with residual gas from pipe 7, before the mixture is fed to turbine 11. By the step of heating in heat exchanger 20, not only is the cold obtained from the throttle expansion 19 transferred to the gaseous fraction in separator 3, but also, just before the mixing operation, a heating of the gaseous fraction above the dew point is performed, so that no condensate formation takes place during the mixing of the gaseous fraction with residual gas fraction 7. In the expansion of the gaseous fraction in throttling valve 19 normally only a small pressure difference, e.g., 1 to 5 bar, is to be spanned, so that here the use of a separate turbine in most cases is not worthwhile from an economical standpoint. On the other hand, in the case of sufficiently large amounts of gas and large pressure differences, e.g., about 3 to 30 bar, the use of an expansion turbine is entirely possible, so as to the increase cooling effect additionally achievable, i.e., the efficiency for raising the yield or for decreasing the external cold requirement.

Before its heating against the crude gas stream in heat exchanger 2, the mixture expanded in turbine 11 is also heated in separator 3 by heat transfer with the gaseous fraction therein. In this way, the desired peak cold obtained in the expansion is transferred to the gaseous fraction, as a result of which the higher hydrocarbons, i.e., the $C_{3+}$, $C_{4+}$ or $C_{5+}$ still contained in it, condense to a particularly great degree, without any subcooling of the condensate removed by pipe 4 taking place at the same time.

In a specific example according to FIG. 2, a refinery gas at a pressure of 29.2 bar and a temperature of 313 K. is introduced into pipe 1. It contains 12.2% hydrogen (indications of percent in each succeeding case refer to mol-%), 36.5 methane, 9.8% ethylene, 13.6% ethane, 13.6% propylene, 4.3% propane, 3.9% $C_{4+}$ hydrocarbons and 6.1% inerts (nitrogen, CO, $CO_2$). After cooling the 220 K. in heat exchanger 2, the gas, at a pressure of 29 bar, is separated from the condensed components. The condensate removed by pipe 4 contains 0.5% hydrogen, 18.2% methane, 14.7% ethylene, 23.2% ethane, 25.6% propylene, 8.1% propane, 7.5% $C_{4+}$ hydrocarbons and 2.2% inerts. It is expanded in valve 17 to the rectification pressure of 27 bar. Rectification is performed in a column having a bottoms temperature of 346 K. and a overhead temperature of 250 K. In this case, in the bottom a $C_{3+}$ product stream collects, which, besides 1% ethane, contains 61.4% propylene, 19.5% propane and 18.1% $C_{4+}$ hydrocarbons. This stream contains 98.6% of the $C_{3+}$ hydrocarbons fed by pipe 1.

A gas stream is removed as overhead product of the rectification, which contains 0.9% hydrogen, 31.0% methane, 25.9% ethylene, 38.8% ethane, 0.5% $C_3$ hydrocarbons and 3.8% inerts. This gas stream is mixed with the gaseous fraction from separator 3, after it has been expanded in throttle valve 19 to a pressure of 27.2 bar and heated in heat exchanger 20 against the unexpanded gaseous fraction.

During the engine expansion of the mixture to a pressure of 6.5, bar the turbine exhaust gas in line 12 cools to a temperature of 191 K. It is then heated against the gaseous fraction in separator 3 to 207 K. and finally heated to 310 K. against the crude gas to be cooled in heat exchanger 2, before it is removed from the system with a pressure of 5.7 bar.

Figure 3:
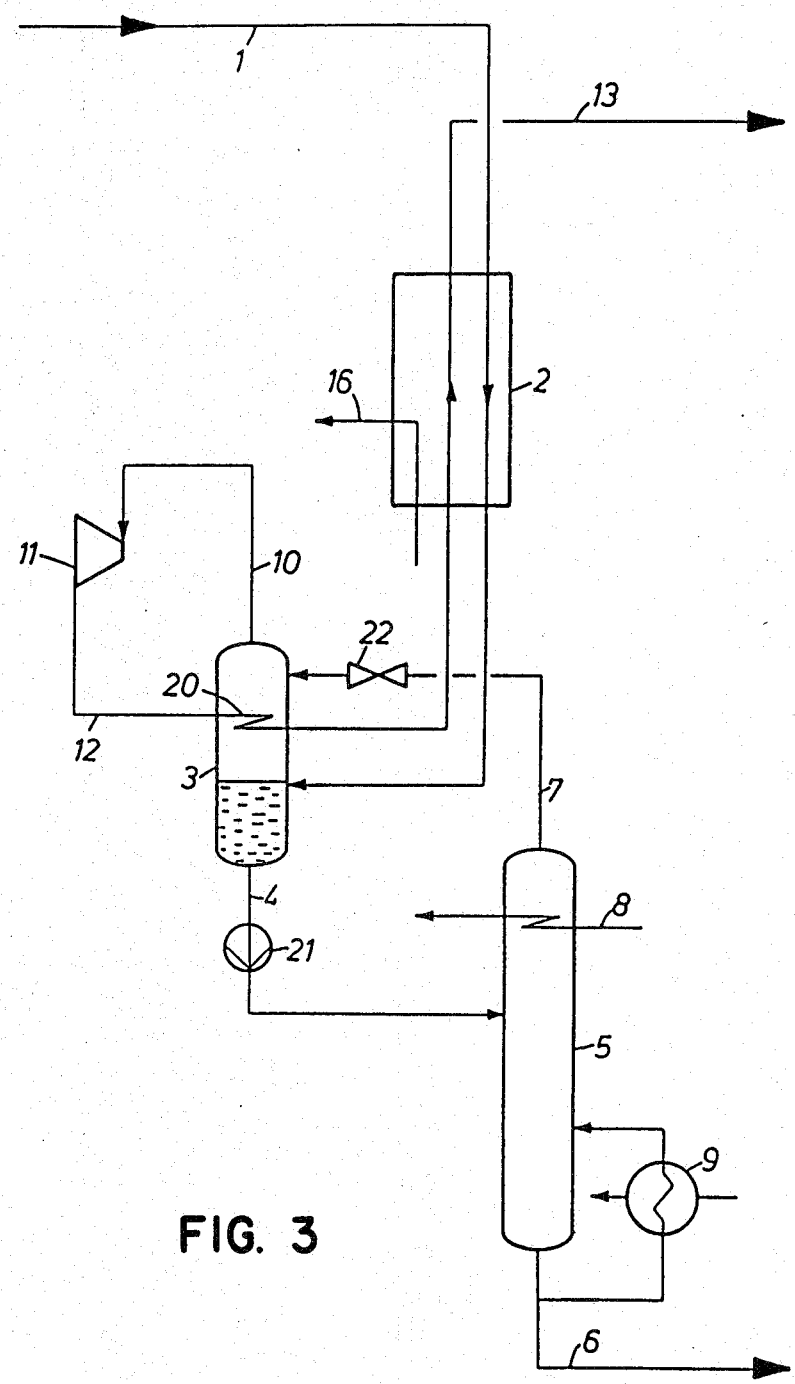
FIG. 3, is another embodiment of the invention, in which the rectification column pressure is higher than the pressure of the mixture to be fractionated.

The embodiment shown in FIG. 3 differs from the embodiment of FIG. 2 substantially through the fact that the rectification is performed under higher pressure, e.g., about 1 to 30 bar than the pressure prevailing in phase separator 3. Therefore, condensate 4 removed from separator 3 is pumped to the elevated rectification pressure by a liquid pump 21. The overhead gaseous product of the rectification stage removed by pipe 7 must, before mixing with the gaseous fraction from separator 3, be expanded to the latter's pressure, for which a throttle valve 22 is so utilized. The expanded overhead product is introduced into separator 3 at a point above heat exchanger 20. The condensate forming during the mixing of these two streams is removed in separator 3, so that a substantially liquid-free mixture is fed by pipe 10 to turbine 11.

In a specific example according to FIG. 3, a refinery gas, which contains 20.1% hydrogen, 31.2% methane, 13.3% ethylene, 16.9% ethane, 5.2% propylene, 1.8% propane, 0.9% $C_{4+}$ hydrocarbons, 0.1% sulfur compounds and 10.5% inerts, is fed at a pressure of 16.2 bar and a temperature of 288 K. into the installation by pipe 1. The gas, from which the $C_{2+}$ hydrocarbons are to be recovered, is cooled in heat exchanger 2 to 175 K. and then fed into phase separator 3 at a pressure of 16 bar.

The condensate removed by pipe 4 is pumped in pump 21 to the rectification pressure of 32 bar and fed into column 5, which is operated at an overhead temperature of 180 K. and a bottom temperature of 285 K. This condensate stream contains 0.3% hydrogen, 20.1% methane, 26.7% ethylene, 35.0% ethane, 10.9% propylene, 3.8% propane, 1.8% $C_{4+}$ hydrocarbons, 0.2% sulfur compounds and 1.2% inerts. A product stream containing only 70 ppm methane as well as 33.8% ethylene, 45.0% ethane, 14.0% propylene, 4.8% propane, 2.2% $C_{4+}$ hydrocarbons and 0.2% sulfur compounds is removed by pipe 6. The $C_2$ yield is 96.6% (relative to the $C_2$ content in gas stream 1 that is to be fractionated). The residual gas of the rectification contains 1.6% hydrogen, 91.0% methane, 2.1% ethylene, 0.3% ethane and 5.0 inerts. It is removed at a temperature of 180 K. by pipe 7, expanded in valve 22 to 16 bar and fed into separator 3. The resulting gas mixture which forms in the upper region of separator 3 at 154° K. is expanded in turbine 11 to a pressure of 8.5 bar, whereby an exhaust gas temperature of 140 K. occurs. This peak cold is transferred by heat exchanger 20 in separator 3 to cool the gaseous fraction, whereupon the resultant expanded gas is fed at a temperature of 170 K. to exchanger 2, before it is finally delivered by pipe 13 at a temperature of 285 K. and a pressure of 7.9 bar.

Figure 4:
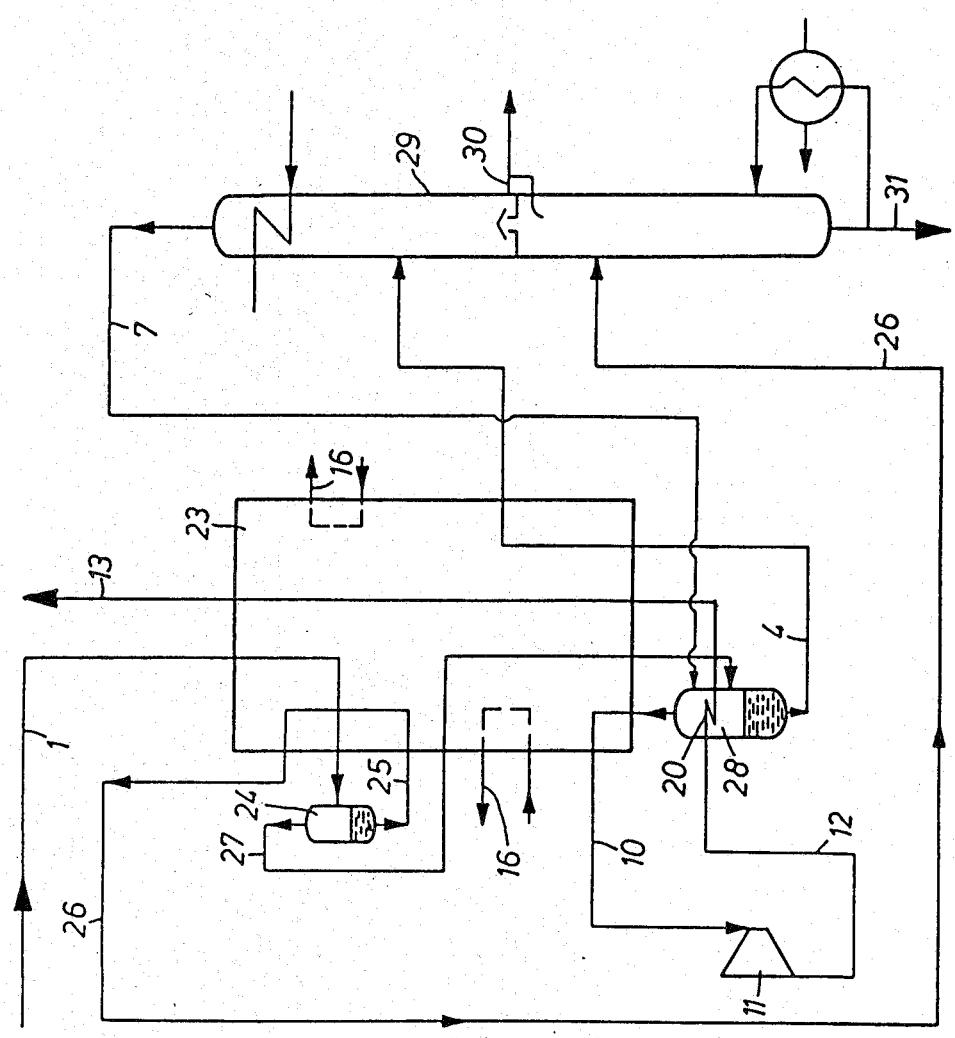
FIG. 4, is an embodiment wherein the $C_{5+}$ hydrocarbons are condensed out upstream and passed separately to the rectification column.

The embodiment represented in FIG. 4 discloses another embodiment of the process in which as a first process step a $C_{5+}$ separation from the incoming gas mixture is performed. For this purpose, feedstock stream 1 is initially cooled in a heat exchanger 23 only enough for most of the $C_{5+}$ hydrocarbons to condense. The partially cooled mixture at an intermediate temperature, e.g., about 240° to 280° K., comes out of heat exchanger 23, is then subjected to a phase separation in a separator 24, whereby the condensed components are separated by pipe 25, removed by pipe 26 after a partial heating in heat exchanger 23, and fed to rectification column 29. The remaining gaseous component of the gas stream is removed from separator 24 by pipe 27, again is cooled in heat exchanger 23 and finally is fed to separator 28, which corresponds to phase separator 3 of the previously described embodiment.

Rectification of the condensates separated in separators 24 and 28 takes place in a separation column 29, which in comparison with the separation column used in the preceding examples, exhibits a greater number, e.g., about 20 to 50, of theoretical plates. Between the two feed pipes 26 and 4, this column is equipped with a draw-off pipe 30 at the particular column location where the highest $C_3/C_4$ concentration is found. In the bottom of column 29, a liquid collects which contains essentially only $C_{5+}$ hydrocarbons and which is removed as product stream by pipe 31. A light fraction, which substantially comprises a $C_1$ and, if desired, $C_2$ hydrocarbon stream, is removed from the overhead of column 29 by pipe 7 as in the preceding examples.

In this process the heavy components, i.e., the $C_{5+}$ fraction, which have been separated in separator 24, are also fed to the rectification stage. In this way, a very high yield of economically desirable $C_3$ and $C_4$ hydrocarbons can be attained at a relatively small expense.

Figure 5:
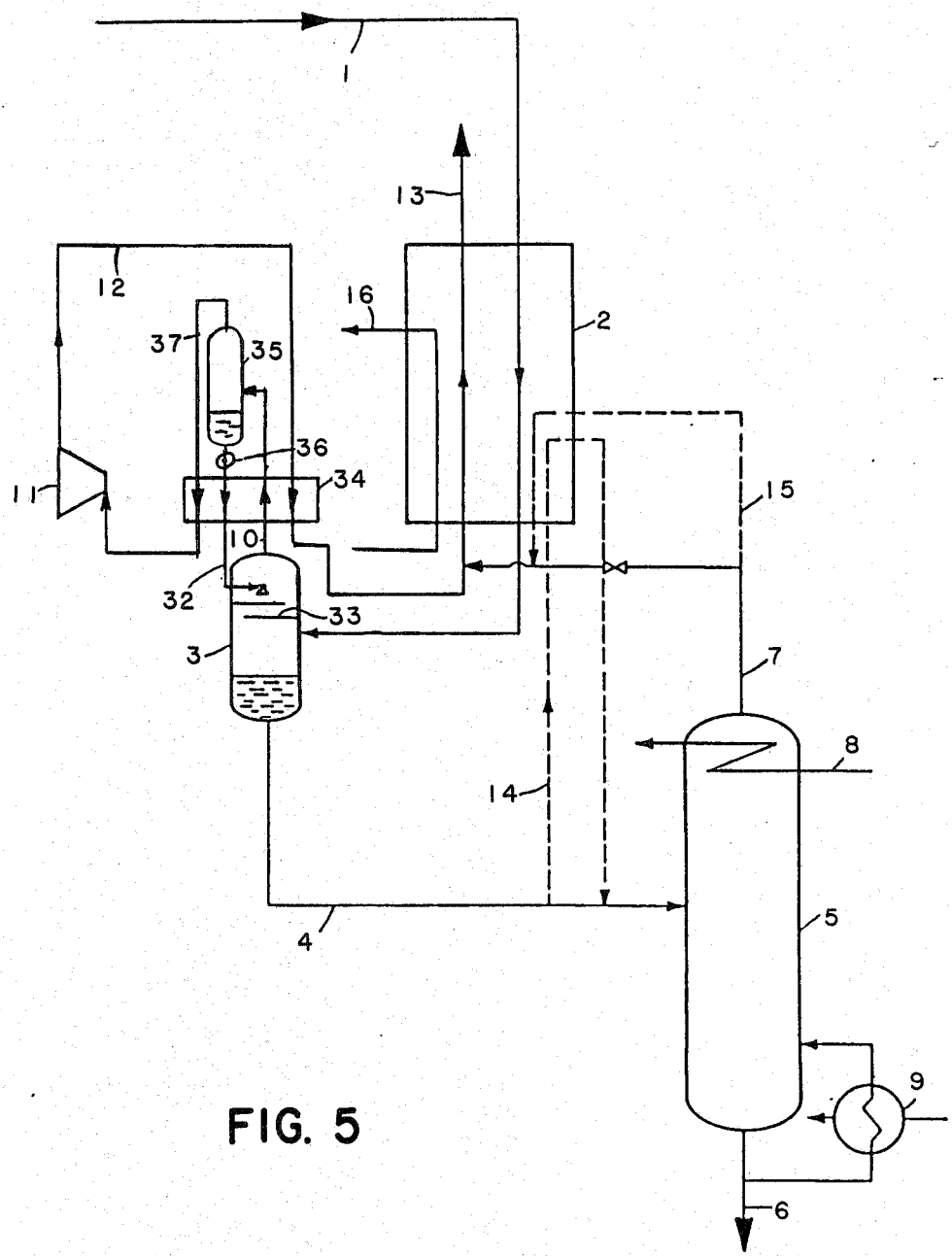
FIG. 5, is another embodiment of the invention in which the components which are condensed out of the gaseous fraction are returned to the phase separator.

In FIG. 5 is represented another embodiment of the invention in which an additional fraction is condensed out from the gaseous fraction and collected in a separate phase separator. To indicate the essential differences in the process, here only the changes in comparison with the process embodiment shown in FIG. 1 are discussed.

After the partial condensation in heat exchanger 2 a phase separation is again performed in separator 3. However, the heat exchanger 20, i.e., the coiled heat exchanger is no longer positioned in the upper region of separator 3. Instead of this, the gaseous fraction which comes into the upper region of the separator enters into a mass transfer column with the countercurrent downward flowing condensate stream brought by pipe 32. To assist in the mass transfer, it is preferred to provide a sufficient number of plates 33, a packing, or the like in this region. The gas removed by pipe 10 from this upper region of separator 3 is cooled in a heat exchanger 34, e.g., a simple plate heat exchanger, wherein still other components condense and are separated in separator 35. The separated condensate is again fed through heat exchanger 34 by a pump 36 which overcomes the pressure losses in the piping, and the condensate is heated to the temperature of separator 3, before it is fed by pipe 32 back into the upper region of separator 3. The component of the gaseous fraction which is uncondensed in heat exchanger 34 is fed to expansion turbine 11 by pipe 37 and there is engine expanded, e.g., to about 120° to 230° K. and 3 to 20 bar. The expanded and cooled gas is removed by pipe 12, transfers its peak cold first in heat exchanger 34 to gaseous fraction 10 and then is heated, e.g., about 270° to 330° K., in heat exchanger 2 against gas that is to be partially condensed, before it is finally removed by pipe 13.

Figure 6:
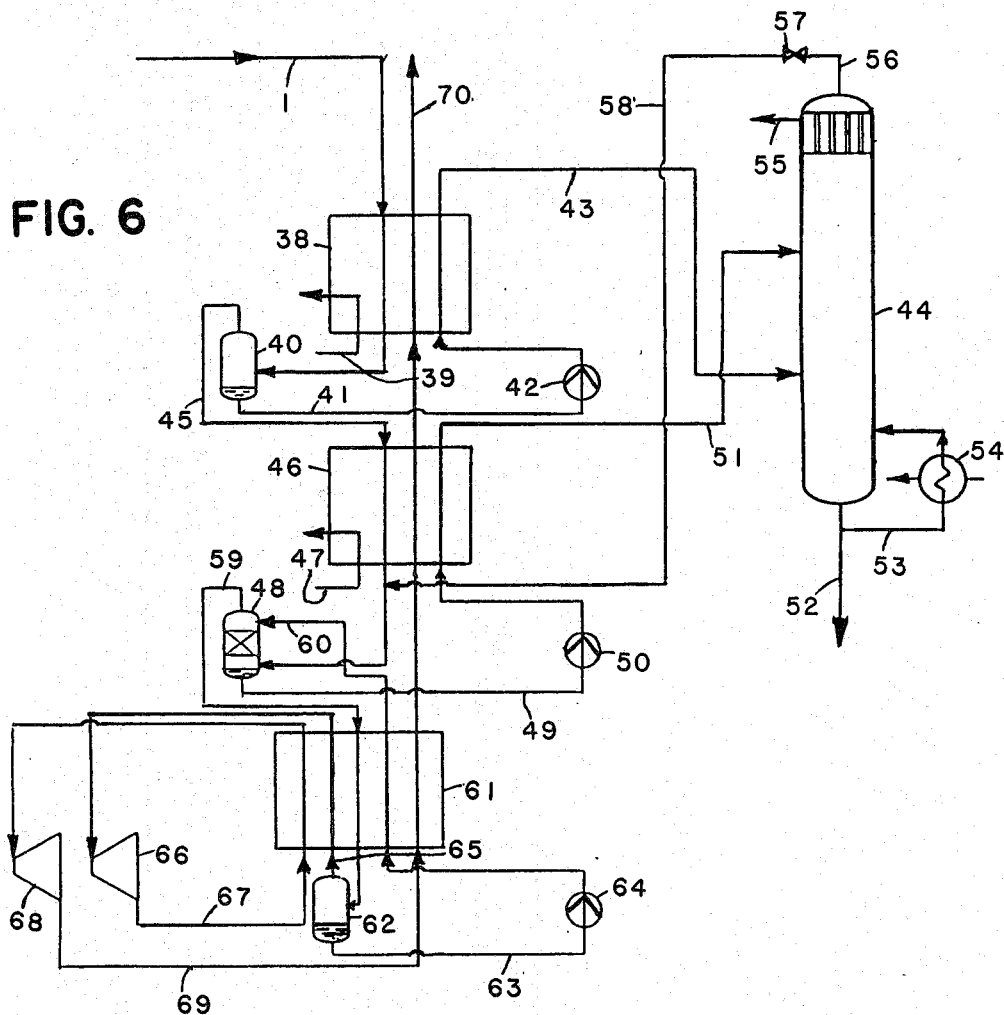
FIGS. 6 and 7, disclose yet two other embodiments of the invention featuring an additional separation of the liquid components that are additionally condensed out of the phase separated gaseous fraction.

The embodiment shown in FIG. 6 is particularly suitable for $C_{2+}$ separation. The gas stream to be fractionated is brought in by pipe 1 at substantially ambient temperature and is first subjected to a two-stage partial condensation, wherein a large part, e.g., about 70 to 96 mol-%, of the $C_{2+}$ hydrocarbons are condensed. First, the feed gas stream is heat exchanger 38 is cooled against external cold 39 and against the process streams that are to be heated and then subjected to a first phase separation in phase separator 40 at 200° to 250° K. and 10 to 40 bar. The separated condensate, which substantially comprises $C_{2+}$ hydrocarbons and contains only small amounts, e.g., about 1 to 20 mol-% of lower boiling components, is removed by pipe 41, conveyed by pump 42 through heat exchanger 38, in which it is again heated against feed gas that is to be cooled, and is transported by pipe 43 into the lower region of a rectification column 44. The remaining, gaseous fraction, is removed from separator 40 by pipe 45, further cooled in another heat exchanger 46 against external cold 47 and/or process streams that are to be heated and then enters into the lower region of phase separator 48. Formed condensate is removed from separator 48 by pipe 49, pumped by pump 50 and heated in heat exchanger 46 against the process streams that are to be cooled, and finally arrives in rectification column 44 by pipe 51. Since this stream contains a larger portion of lower boiling components than the stream brought by pipe 43, the feed into rectification column 44 takes place at a higher column location, the precise location being determined according to the particular equilibrium of the composition. A $C_{2+}$ fraction of the lower boiling components is substantially separated in the rectification column and removed from the bottoms by pipe 52. Part of the bottoms product is taken off by pipe 53, heated in heat exchanger 54 and returned as bottoms heating into the lower region of the column. At the head of rectification column 44, cooled to 160° to 200° K. by external cold 55, a fraction containing substantially only methane and lower boiling components is removed by pipe 56. After expansion to he crude gas pressure in valve 57, the overhead product is returned into the crude gas by pipe 58 and mixed with the gaseous fraction removed from separator 40, after this fractin had been again cooled in heat exchanger 46, passing through separator 48. The gaseous fraction forming in separator 48, i.e., the fraction that contains both the portion of the gaseous fraction from separator 40 that has not condensed in heat exchanger 46 and the overhead product 56 of rectification column 44, is removed at the upper end of separator 48 by pipe 59. In separator 48 it enters into a countercurrent mass transfer with a condensate fraction described below, and maintained substantially at boiling temperature, e.g., about 150° to 200° K., brought in by pipe 60. The gaseous fraction removed by pipe 59 is then cooled, e.g., about 130° to 180° K. and partially condensed in a heat exchanger 61, e.g., preferably a plate heat exchanger, by heat transfer with the peak cold formed in a downstream engine expansion, infra. The additional condensate formed therein is separated in a separator 62, removed by pipe 63 and conveyed by pump 64 through heat exchanger 61, in which it is again heated to about its boiling temperature, and finally fed by pipe 60 into the upper region of separator 48. The gaseous fraction from separator 62 is fed by pipe 65 to heat exchanger 61 and after heating, is engine expanded in two stages. Thus, a first engine expansion 66 is performed and the partially expanded gas, e.g., at 8 to 30 bar and 125° to 175° K., is again heated in heat exchanger 61 by pipe 67 before it is again expanded in the expansion engine, i.e., turbine 68. The expanded cold gas is finally removed by pipe 69 and while passing through heat exchangers 61, 46 and 38, being heated against the process streams that are to be cooled, then leaving the installation by pipe 69 as a light gas fraction, e.g., at about 270° to 330° K. and 3 to 20 bar.

In a specific example, according to FIG. 6, a gas is brought in by pipe 1 at a temperature of 313 K. and under a pressure of 21 bar, which contains 22.5% hydrogen, 30.9% methane, 23.7% $C_2$ hydrocarbons, 6.8% $c_3$ hydrocarbons, 12.5% $C_{4+}$ hydrocarbons and 3.6% residual components (substantially nitrogen and carbon monoxide, as well as small amounts of carbon dioxide and oxygen). After cooling to 237 K., a first condensate is separated in separator 40, a condensate that, in addition to the $C_{2+}$ hydrocarbons, now contains only 7.6% methane and 0.5% hydrogen, as well as 0.4% residual components. The remaining gas phase is cooled in heat exchanger 46 to a temperature of 176 K. and, after mixing with the overhead product of the rectification in stream 48, which contains 2.6% hydrogen, 92.5% methane, 2.4% $C_2$ hydrocarbons and 2.5% residual components, is fed into separator 48. The gaseous fraction, removed from separator 48 by pipe 59, contains 35.1% hydrogen, 55.9% methane, 3.5% $C_2$ hydrocarbons and 5.6% residual components. It collects at a temperature of 169 K. and is cooled in heat exchanger 61 to 155 K., thereby forming a condensate which contains 1.0% hydrogen, 73.8% methane, 23.1% $C_2$ hydrocarbons and 2.1% residual components and which, after renewed heating in heat exchanger 61, is delivered to the head of separator 48 at 166 K. and 20.4 bar. Before being fed to separator 48, the aforementioned condensate is heated to at least boiling temperature at 166 K., but is still predominantly present as a liquid. The gaseous fraction which collects in separator 62, and then engine expanded and finally delivered as a residual gas fraction 69, contains 39.5% hydrogen, 53.6% methane, 0.9%

$C_{2+}$ hydrocarbons and 6.0% residual components. In rectification column 44, in addition to the overhead fraction mentioned, supra, a bottoms product is taken off by pipe 52, comprising 0.8% methane, 54.0% $C_2$ hydrocarbons, 15.8% $C_3$ hydrocarbons, 29% $C_{4+}$ hydrocarbons and 0.4% residual components. It is removed at a bottoms temperature of 304 K. from the rectification column, which is operated at a pressure of 30 bar. This stream contains 98.8% of the $C_{2+}$ hydrocarbons introduced into the installation by pipe 1.

Figure 7:
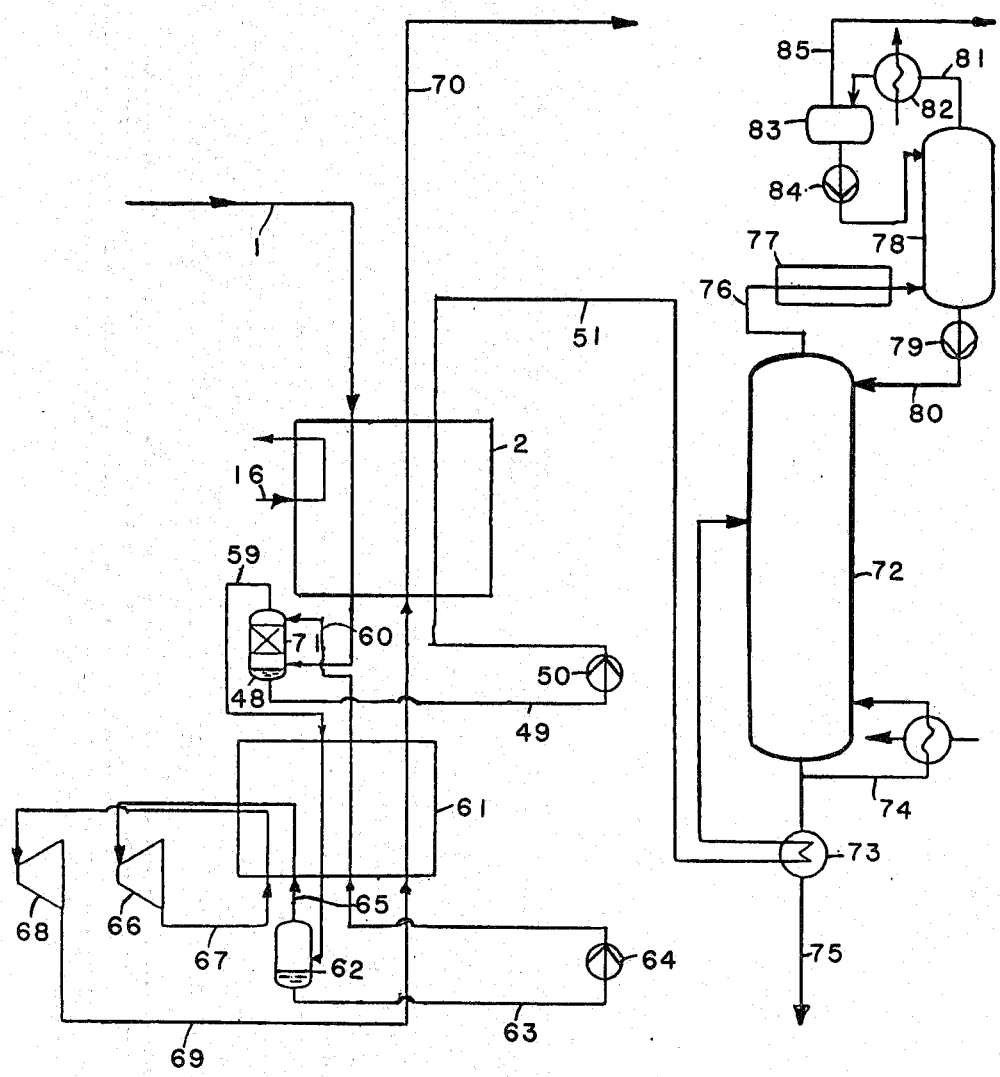

In a further embodiment of the invention disclosed in FIG. 7, as in the case of the process set forth in FIG. 6, a further and separate separation of additionally condensed components is performed. The embodiment shown in FIG. 7 is particularly suitable for a separation of the $C_{4+}$ hydrocarbons. The performance of the process corresponds substantially to that of FIG. 6, except for the differences described below.

The crude gas stream fed by pipe 1 is partially condensed in one stage; therefore, after flowing through heat exchanger 2, it enters separator 48 without mixing with another fraction. The resulting gaseous fraction collecting in separator 48 after flowing through rectification section 71, is removed by pipe 59 and, is further processed in accordance with the embodiment of FIG. 6, the variation consisting of the fact that the gaseous fraction removed from separator 62 by pipe 65 before its engine expansion in both passes flows through only a part of heat exchanger 61, i.e., it is not heated to the input temperature of heat exchanger 61, e.g., about 220 to 250 K., but rather, to about 200 to 230 K. The condensate fraction is removed from separator 48 by pipe 49, pumped to the pressure of rectification column 72 and, after being heated in heat exchanger 2, before feeding into the rectification column is again heated in heat exchanger 73 against the bottoms product of the rectification column. While a partial stream 74 of the bottoms product is heated and again fed into the column bottoms, the remaining bottoms product leaves through pipe 75 as $C_{4+}$ product fraction. The overhead from rectification column 72 is a $C_3$-fraction which is removed by pipe 56, cooled in heat exchanger 77 and partially condensed. In this case, ambient air can be used as the coolant. The condensed portion is separated in the lower section of the rectification column 78 and is conveyed as a reflux stream by pump 79 and pipe 80 back to the top of rectification column 72. The remaining uncondensed portion is carried by pipe 81 into a cooler 82, wherein additional components condense. The condensate thus formed is separated in another phase separator 83 and is returned by pump 84 into the upper region of column 78. A $C_3$-hydrocarbon fraction is removed as another product fraction from separator 83 by pipe 85.

In a specific example corresponding to FIG. 7, a crude gas enters pipe 1 at a temperature of 313 K. and under a pressure of 12 bar is fed into heat exchanger 2 and cooled there to 234 K. The gaseous fraction removed by pipe 59 from separator 48 at a temperature of 233 K. contains 80.8% hydrogen, 15.5% methane, 0.7% $C_2$ hydrocarbons, 0.5% $C_3$ hydrocarbons and 2.5% $C_4$ hydrocarbons. After cooling to 190 K. in heat exchanger 61 a condensate collects in pipe 63, which contains 0.4% hydrogen, 3.2% methane, 4.0% $C_2$ hydrocarbons, 12.7% $C_3$ hydrocarbons and 79.5% $C_4$ hydrocarbons. After heating to 230 K., it is carried by pipe 60 into the upper region of separator 48. At this point, it is essentially at its boiling temperature, but substantially present in the liquid state. The gaseous fraction removed from separator 62 contains 83.3% hydrogen, 15.9% methane, 0.6% $C_2$ hydrocarbons and 0.1% each of $C_3$ and $C_4$ hydrocarbons. The engine expanded gaseous fraction contains only about 0.2% of the $C_4$ hydrocarbons contained in pipe 1, while the condensate removed from separator 48 contains 0.5% hydrogen, 1.6% methane, 1.0% $C_2$, 4.4% $C_3$ and 92.5% $C_4$ hydrocarbons and is further fractionated in rectification column 72.

The preceding examples can be repeated with similar success by substituting the generally or specifically described components and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the separation of $C_{2+}$, $C_{3+}$ or $C_{4+}$ hydrocarbons from a gas stream containing light hydrocarbons in which the gas stream, being under an elevated pressure, is cooled, partially condensed and separated in a phase separator into a liquid and a gaseous fraction; the fraction is engine expanded, and the liquid fraction is fractionated by rectification into a product stream containing substantially $C_{2+}$, $C_{3+}$ or $C_{4+}$ hydrocarbons and a residual gas stream containing predominantly lower boiling components, the improvement comprising subjecting the gaseous fraction forming after partial condensation, before engine expansion thereof, to heat exchange with the engine expanded gaseous fraction, thereby cooling said gaseous fraction and separating additional components which condense out before the engine expansion stage.

2. A process according to claim 1, wherein the heat exchange between the unexpanded and expanded gaseous fractions occurs in a column having at least two equilibrium stages, in which the phase separation of the liquid fraction formed during the partial condensation is also performed, wherein the partially condensed gaseous fraction is fed into the lower region of the column and the heat exchange between the unexpanded and expanded gaseous fraction substantialy occurs in the upper region of the column.

3. A process according to claim 1, wherein during the additional cooling of the gaseous fraction, the additional components condensed out are separated from the gaseous fraction and returned to said phase separator.

4. A process according ot claim 3, wherein the additional components condensed out are fed into the upper region of the phase separator and passed through the phase separator countercurrent to the rising gaseous fraction.

5. A process according to claim 4, wherein the additional components condensed out are at least in part reheated before being returned into the separator.

6. A process according to claim 5, wherein the heating involves raising the additional condensed out components at least to the boiling point.

7. A process according to claim 1, wherein the residual gas stream collecting during rectification is fed into and mixed with the gaseous fraction collecting after partial condensation; the resulting mixture is engine expanded and then heated by heat exchange with the gas stream that is to be fractionated.

8. A process according to claim 7, wherein the condensate formed during mixing is separated before the engine expansion.

9. A process according to claim 8, wherein the residual gas formed as a product of the rectification is fed in the column for the separation of the liquid from the gaseous fraction.

10. A process according to claim 1, wherein before the rectification, the liquid fraction is at least in part heated to a desired temperature against the gas stream that is to be cooled.

11. A process according to claim 1, wherein during processing of the gas stream, in which a substantial amount of components boiling lower than methane are present, a gaseous fraction is substantially separated from these $C_1/C_2$ hydrocarbons by partial condensation, before the engine expansion of the gaseous fraction.

12. A process according to claim 1, wherein a substantial amount of the $C_{5+}$ hydrocarbons, which may be present in the gas stream, are separated before the formation of the liquid and gaseous fractions.

13. A process according to claim 12, wherein the separated $C_{5+}$ hydrocarbons are also fed to the rectification column, with the feed containing the $C_{5+}$ component entering the rectification column before the feed of the liquid fraction formed during partial condensation, and a product stream containing substantially $C_3$ and $C_4$ hydrocarbons is removed from the column at a location between the two feeds.

14. A process as claimed in claim 1, wherein the residual gas from the rectification stage has a higher molecular weight than the gaseous fraction.

15. A process according to claim 2, wherein the residual gas stream collecting during rectification is fed into and mixed with the gaseous fraction collecting after partial condensation; the resulting mixture is engine expanded and then heated by heat exchange with the gas stream that is to be fractionated.

16. A process according to claim 3, wherein the residual gas stream collecting during rectification is fed into and mixed with the gaseous fraction collecting after partial condensation; the resulting mixture is engine expanded and then heated by heat exchange with the gas stream that is to be fractionated.

17. A process according to claim 7, wherein before the rectification, the liquid fraction is at least in part heated to a desired temperature against the gas stream that is to be cooled.

18. A process according to claim 15, wherein before the rectification, the liquid fraction is at least in part heated to a desired temperature against the gas stream that is to be cooled.

19. A process according to claim 7, wherein a substantially amount of the $C_{5+}$ hydrocarbons, which may be present in the gas stream, are separated before the formation of the liquid and gaseous fractions.

20. A process according to claim 17, wherein a substantial amount of the $C_{5+}$ hydrocarbons, which may be present in the gas stream, are separated before the formation of the liquid and gaseous fractions.

21. A process according to claim 1 wherein the gas stream containing light hydrocarbons further comprises components boiling lower than methane.

22. A process according to claim 1 wherein the rectification occurs at a temperature in the overhead condenser of about 160–300 K.

* * * * *

UNITED STATES PATENT AND TRADEMARK OFFICE
CERTIFICATE OF CORRECTION

PATENT NO. : 4,664,687

DATED : 5-12-87

INVENTOR(S) : Heinz Bauer

It is certified that error appears in the above-identified patent and that said Letters Patent is hereby corrected as shown below:

Column 14, Claim 19, Line 21-21:

Reads: "19. A process according to claim 7, wherein a substantially"

should read: --19. A process according to claim 7, wherein a substantial--

Signed and Sealed this

Eighteenth Day of August, 1987

Attest:

DONALD J. QUIGG

*Attesting Officer*       *Commissioner of Patents and Trademarks*